US009241891B2

(12) United States Patent
Whitehouse et al.

(10) Patent No.: US 9,241,891 B2
(45) Date of Patent: Jan. 26, 2016

(54) PERSONAL CARE COMPOSITIONS COMPRISING SELF-ASSEMBLING PEPTIDES

(71) Applicant: The Procter & Gamble Company, Cincinnati, OH (US)

(72) Inventors: Conor David Whitehouse, Egham (GB); Ellen Schmidt Baker, Cincinnati, OH (US); Ioannis Constantine Constantinides, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 116 days.

(21) Appl. No.: 14/065,865

(22) Filed: Oct. 29, 2013

(65) Prior Publication Data

US 2014/0120042 A1    May 1, 2014

Related U.S. Application Data

(60) Provisional application No. 61/720,264, filed on Oct. 30, 2012.

(51) Int. Cl.
| *A61K 8/02* | (2006.01) |
| *A61K 8/64* | (2006.01) |
| *A61Q 5/12* | (2006.01) |
| *A61Q 19/00* | (2006.01) |
| *A61Q 5/00* | (2006.01) |
| *A61Q 1/10* | (2006.01) |
| *A61Q 17/04* | (2006.01) |
| *A61Q 19/02* | (2006.01) |
| *A61Q 5/06* | (2006.01) |
| *A61Q 19/08* | (2006.01) |

(52) U.S. Cl.
CPC . *A61K 8/64* (2013.01); *A61K 8/027* (2013.01); *A61Q 1/10* (2013.01); *A61Q 5/00* (2013.01); *A61Q 19/00* (2013.01); *A61K 2800/10* (2013.01); *A61K 2800/548* (2013.01); *A61K 2800/56* (2013.01); *A61K 2800/884* (2013.01); *A61K 2800/92* (2013.01); *A61K 2800/95* (2013.01); *A61Q 5/06* (2013.01); *A61Q 5/12* (2013.01); *A61Q 17/04* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 5,955,343 | A | 9/1999 | Holmes et al. |
| 6,548,630 | B1 | 4/2003 | Zhang et al. |
| 6,800,481 | B1 | 10/2004 | Holmes et al. |
| 7,098,028 | B2 | 8/2006 | Holmes et al. |
| 7,906,478 | B2 | 3/2011 | Carlucci |
| 8,063,014 | B2 | 11/2011 | Stupp |
| 2004/0018961 | A1 | 1/2004 | Stupp et al. |
| 2004/0057920 | A1 | 3/2004 | Focht |
| 2004/0132667 | A1 | 7/2004 | Lintne |
| 2005/0181973 | A1 | 8/2005 | Genove et al. |
| 2005/0272662 | A1 | 12/2005 | Stupp et al. |
| 2006/0149036 | A1 | 7/2006 | Stupp et al. |
| 2007/0190603 | A1 | 8/2007 | Holmes et al. |
| 2007/0203062 | A1 | 8/2007 | Ellis-Behnke et al. |
| 2008/0020637 | A1 | 1/2008 | Montena |
| 2008/0075798 | A1 | 3/2008 | Osborne |
| 2008/0199431 | A1 | 8/2008 | Capito |
| 2008/0299657 | A1 | 12/2008 | Stupp et al. |
| 2009/0010972 | A1 | 1/2009 | Fari |
| 2009/0029900 | A1 | 1/2009 | Cetti et al. |
| 2009/0111734 | A1 | 4/2009 | Ellis-Behnke |
| 2009/0162437 | A1 | 6/2009 | Horii et al. |
| 2009/0269847 | A1 | 10/2009 | Stupp |
| 2009/0297579 | A1 | 12/2009 | Semino et al. |
| 2009/0317167 | A1* | 12/2009 | Pires et al. .............. 401/65 |
| 2010/0016548 | A1 | 1/2010 | Yokoi et al. |
| 2010/0034574 | A1* | 2/2010 | Zhang .................. 401/47 |
| 2010/0189669 | A1 | 7/2010 | Hakozaki |
| 2010/0227011 | A1 | 9/2010 | Kuhlman |
| 2010/0239510 | A1 | 9/2010 | Ha |
| 2011/0008890 | A1 | 1/2011 | Stupp et al. |
| 2012/0014925 | A1 | 1/2012 | Kumada et al. |

FOREIGN PATENT DOCUMENTS

| WO | WO9701313 | 1/1997 |
| WO | WO00/62743 | 10/2000 |
| WO | WO03/084980 | 10/2003 |
| WO | WO2004/007532 | 1/2004 |
| WO | WO2005/014615 | 2/2005 |
| WO | WO2005/057163 | 6/2005 |
| WO | WO2006/116524 | 11/2006 |

(Continued)

OTHER PUBLICATIONS

Ellis-Behnke et al. Nano hemostat solution: immediate hemostasis at the nanoscale. Nanomedicine: Nanotechnology, Biology, and Medicine. 2006, vol. 2, No. 4, pp. 207-215.*
Aggeli, A et al."Self Assembling Peptide Polyelectrolyte B-Sheet Complexes Form Nematic Hydrogels" *Angew. Chem. Int. Ed.* 2003, 42, 5603-5606.
Aggeli, A. et al. Hierarchical self-assembly of chiral rod-like molecules as a model for peptide B-sheet tapes, ribbons, fibrils, and fibers.; *PNAS* 2001, 98, 11857-11862.
Capito, R. et al. "Self Assembly of Large and Small Molecules into Hierarchically Ordered Sacs and Membranes";Science 2008, 319, 1812-1816.
Fletcher, N. et al., "A pH-responsive coiled-coil peptide hydrogel" *Soft Matter* 2011, 7, 10210-10218.

(Continued)

*Primary Examiner* — Jeffrey E Russel
(74) *Attorney, Agent, or Firm* — John G. Powell

(57) ABSTRACT

Disclosed herein are personal care compositions having at least one oligopeptide self-assembled into nanofibers or macrostructures, wherein the oligopeptide is 2-20 amino acids in length, and wherein the oligopeptide has at least one 0- to 10-amino-acid block of hydrophobic amino acids alternating with at least one 1- to 10-amino-acid block of hydrophilic amino acid residues. The composition may further include a dermatologically acceptable carrier and at least one cosmetic skin care agent.

15 Claims, No Drawings

(56) References Cited

FOREIGN PATENT DOCUMENTS

| WO | WO2008/101104 | 8/2008 |
| WO | WO2008/113030 | 9/2008 |
| WO | WO2008/127256 | 10/2008 |
| WO | WO2012/008967 | 1/2012 |

OTHER PUBLICATIONS

Hamley, I. "Self Assembly of Amphiphilic peptides"; *Soft Matter*, 2011, 7, 4122-4138.

Kao, B et al., "Construction of Synthetic Dermis and Skin Based on a Self-Assembled Peptide Hydrogel Scaffold" Tissue Engineering, 15:2385-2396, 2009.

Reches, M. et al."Molecular Self Assembly of Peptide Nanostructures: Mechanism of Association and Potential Uses" *Curr. Nanoscience* 2006, 2, 105-111.

Whitehouse, C. et al; "Adsorption and Self-Assembly of Peptides on Mica Substrates" *Angew. Chem. Int. Ed.* 2005, 44, 1965-1968.

Whitesides, G. et al.; "Molecular Self-Assembly and Nanochemistry: A Chemical Strategy for the Synthesis of Nanostructures" *Science* 1991, 254, 1312-1319.

Zhang, S. et al. "A Self-Assembly Pathway to Aligned Monodomain Gels", Nature Materials 2010, 9, 594-601.

Matson, J.B., et al. "Peptide self-assembly for crafting functional biological materials" Current Opinion in Solid State and Materials Science vol. 15(6), 2011 p. 225-235.

Castelletto, V. et al. "Self-Assembly of Palmitoyl Lipopeptides Used in Skin Care Products Valeria Castelletto", Langmuir 2013, 29 (29) 9149-9155.

Meng, H. et al. "The Effect of a Self-Assembling Peptide Nanofiber Scaffold Peptide When Used as a Wound Dressing for the Treatment of Deep Second Degree Burns in Rats" Journal of Biomedical Materials Research, Part B: Applied Biomaterials (2009), 89B(2), 379-391.

International Search Report PCT/US2013/067409; Mailing Date Oct. 30, 2013; 14 pages.

Ellis-Behnke, R. et al., "Nano hemostat solution: Nanomedicine immediate hemostasis at the nanoscale" in Nanomedicine: Nanotechnology, Biology, and Medicine (New York, NY, United States) (2006), 2(4), 207-215.

\* cited by examiner

PERSONAL CARE COMPOSITIONS COMPRISING SELF-ASSEMBLING PEPTIDES

FIELD

The disclosure relates to the field of personal care compositions. More particularly, the disclosure relates to the field of personal care compositions comprising at least one self-assembling peptide.

BACKGROUND

The field of self-assembling peptides (SAP) is an emerging technology area whose rapid growth is fueled by the potential for applications in tissue engineering, biotechnology, nano- and regenerative medicine, nanoengineering, synthetic biology, and optics and electronics. The peptides self assemble to create nanostructures that can promote biological activity (such as nerve regeneration, bone growth, and angiogenesis); enhance active delivery or release; modify liquid rheological properties; and coat or modify surfaces. Additionally, they can create even larger micro- and macrostructures such as membranes, fibrils, fibers and potentially even fabrics.

Molecular self-assembly may be defined as the spontaneous and reversible organization of molecular units into ordered structures, driven by non-covalent interactions (Whitesides et al.; *Science* 1991, 254, 1312-1319). The spontaneous nature of self-assembly processes requires a lowering of the free energy of the system and therefore the formation of the nanostructure from monomer units is commonly associated with a critical concentration of monomer units for self-assembly (Aggeli et al.; *PNAS* 2001, 98, 11857-11862). Prior to the critical concentration, the chemical potential of the monomer species rises rapidly as monomer is added to the system until the critical concentration where the nanostructure starts to form. Above the critical concentration all further monomer added to the system will add to and enlarge the nanostructures with the chemical potential of the monomer species effectively fixed at a set value.

There are multiple secondary structures that are known to form, including extended beta strands (cross-beta structure) that form tapes, tubes and fibers driven by hydrogen bonding parallel to the tape axis, and alpha-helices which form triple-helix collagen-like structures and coiled-coil bundles through side-chain interactions perpendicular to the fiber axis. Of these beta-sheet self-assembly is acknowledged to be the simplest form, where self-assembly is typically driven by a combination of hydrogen bonds, complimentary charge, aromatic and Van der Waals interactions between the monomer peptide residues. Each residue can be estimated to contribute approximately 2-3 kT of free energy to the system, where 1 kT is equal to the amount of thermal energy that is present in a chemical system at room temperature and pressure. Simplistically, therefore any structure which has more than 1 kT in free energy is likely to form thermodynamically-stable structures and the greater this value the more stable and long-lived these structures will be in the chemical system. As a result short peptides are observed to form very large stable self-assembled structures in solution, at interfaces and on surfaces. Remarkably, even dipeptides containing only two amino acids have been shown to self-assemble into beta-sheet peptide tapes that are hundreds of microns in length (Reches and Gazit; *Curr. Nanoscience* 2006, 2, 105-111). More generally, self assembling oligopeptide structures fall into two major classifications: those consisting of sequences of hydrophobic and hydrophilic amino acids which result in amphiphilic properties (an amphiphilic peptide), and those where the amphiphilic properties are the result of modification of the peptide with a hydrophobic group (a peptide amphiphile).

The work of Aggeli, Zhang and Stupp among others has allowed a rational set of design criteria to be defined for self-assembling beta-sheet tape forming peptides and peptide amphiphiles, which allows the skilled practitioner to design and create new self-assembling peptide sequences with reasonable confidence. Based on these seminal studies, it can be seen that in general, increasing the number of residues will decrease the critical concentration as self-assembly becomes more favorable through the increased number of complimentary interactions between the monomer peptides. Solvent conditions including pH, salt concentration, dielectric and temperature have been shown to have significant influence upon the self-assembly behavior dependent on the primary sequence. For oligopeptides containing several charged residues, where there is significant coulombic repulsion between the monomeric peptides, raising the salt concentration will more efficiently screen and neutralize like-charges between monomers and lower the critical aggregation concentration. This is observed with the behavior of the RADA peptides where contact of monomeric solution with higher salt concentration causes instant gelation (Ellis-Behnke et. al.; *Nanomedicine: Nanotechnology, Biology and Medicine* 2006, 2 (4), 207-215). Similarly, pH has significant influence on the self-assembly of oligopeptides containing charged residues, where in general for self-assembly of anionic peptides when the pH is lowered below the pK of the anionic residues, the net charge on the monomeric peptides will be neutralized and the critical aggregation concentration will be lowered. Similarly for self-assembly of cationic peptides when the pH is raised above the pK value of the cationic residues, the net charge is neutralized and the critical aggregation concentration will be lowered (Aggeli et al.; *Angew. Chem. Int. Ed.* 2003, 42, 5603-5606). Commonly most self-assembling peptides would contain a mixture of anionic and cationic charged residues in which case the specific response to pH and salt concentration will be sequence dependent. Additionally it should be recognized that this responsive behavior can be engineered by designing specific sequences that spontaneously self-assemble in the presence of specific environmental conditions such as an increase in salt concentration due to contact with body fluids or sweat insults or change in pH due to contact with keratinous substrates such as skin or hair.

Another significant class of self assembling oligopeptides is the group of peptide amphiphiles, wherein the peptide has been functionalized with an alkyl group (C12-C22). (Hamley; *Soft Matter,* 2011, 7, 4122-4138) Examples of this class of materials have been described to self-assemble in aqueous media, with or without the presence of polymeric compounds, to give nanofibers that can further aggregate to form strong and flexible macrofibers that can be multiple centimeters in length (Capito, et. al.; Science 2008, 319, 1812-1816). These nanofibers can be induced by changing (1) the salt concentration, (2) the pH, or (3) the moisture content of the system. They can be used for various medical applications such as drug delivery, medical diagnostic components, tissue, cartilage, enamel or nerve regeneration, cell growth promotion, and wound healing. Temperature effects have also been extensively explored within the literature and recently were shown by Stupp and coworkers to be of significant importance for affecting subtle rearrangement of self-assembled peptide structures producing significant changes to the rheological behavior and stability of the peptide structures (Zhang et al., *Nature Materials* 2010, 9, 594-601). A heat pre-treatment of the peptide amphiphile solution was used followed by equilibration to lower temperature. This promoted a reorganisation of the self-assembled structure and allowed for formation of aligned nanofiber bundles, creating macrofibers on the order of centimeters long, which were stabilized by exposure to calcium salt solutions.

Similarly studies on collagen mimics and coiled coil peptide sequences have shown that environmental conditions can be used to control the self-assembly process enabling a large range of applications where responsive behavior is required or desired (Fletcher et al., *Soft Matter* 2011, 7, 10210; O'Leary et al.; *Nature Chemistry* 2011, 3, 821-828).

These examples demonstrate how self-assembly behavior can be engineered for specific applications based upon rational design of the primary sequence which in turn determines the macroscopic physical properties of the self-assembled materials. However predicting responsive behavior or the exact critical aggregation concentration for a given oligopeptide cannot be done purely from a knowledge of the primary sequence. Additionally, the peptide will behave differently as solution conditions of pH, ionic strength, temperature, and co-ingredients vary, which will affect the concentration of oligopeptide required to form self-assembled nanofibers in different compositions to achieve the desired behaviour under different application conditions. It can be said that in general: increasing the number of residues will decrease the critical concentration and self-assembly will become more favorable; raising the salt concentration will more efficiently screen like-charges between monomers and lower the critical concentration; and decreasing the temperature will have a similar effect. Thus for purely thickening a composition, a ten residue peptide would typically be present at a lower concentration than a three residue peptide as the ten residue peptide is likely to be more efficient at increasing the viscosity.

As another example Zhang and Ellis-Behnke have shown that application of RADA16-I (SEQ ID NO: 1) to open wounds can instantly stop bleeding (Haemostasis) through salt-induced peptide self-assembly to form fibrous hydrogel transparent membranes that encapsulate and prevent further blood loss from the wound (Ellis-Behnke et. al. *Nanomedicine: Nanotechnology, Biology and Medicine* 2006, 2 (4), 207-215). These membranes can be envisioned to provide a variety of other benefits in personal care compositions such as skin protection, active delivery, wrinkle reduction, and wetness protection. Skin actives require penetration into the skin in order to function. The thermodynamic favorability of penetration is critical. For that reason, the concentration of the material in the composition must be near the saturation point for optimum penetration. The most significant cost in producing a composition comprising a skin active is the cost of producing or obtaining the skin active itself. Thus, there is a need in the arts of cosmetic and pharmaceutical compositions applied to the skin to efficiently deliver a skin active to, into, and/or through the skin, which could be enabled by incorporation of self assembling peptides.

Notwithstanding these developments, a need continues to exist to develop compositions, and methods of using those compositions, that provide improved or new benefits via personal care compositions comprising self assembled peptides, for example to improve the delivery of skin or hair benefit agents to the skin or hair, to provide hair and skin surface modification, or to create elongated hair fibers.

SUMMARY OF THE DISCLOSURE

In one aspect, described herein is a personal care composition comprising having at least one oligopeptide self-assembled into nanofibers or macrostructures, wherein the oligopeptide is 2-20 amino acids in length, and wherein the oligopeptide has at least one 0- to 10-amino-acid block of hydrophobic amino acids alternating with at least one 1- to 10-amino-acid block of hydrophilic amino acid residues. The composition may further include a dermatologically acceptable carrier and at least one cosmetic skin care agent.

Additional aspects, features and variations of the disclosure will be apparent from the entirety of this application, including the detailed description, and all such features are intended as aspects of the disclosure. It should be understood, however, that the detailed description and the specific examples are given by way of illustration, and that the many various changes and modifications that will be apparent to those familiar with the field of the disclosure are also part of the disclosure.

Aspects of the disclosure described with the term "comprising" should be understood to include the elements explicitly listed and, optionally, additional elements. Aspects of the disclosure described with "a" or "an" should be understood to include "one or more" unless the context clearly requires a narrower meaning.

With respect to aspects of the disclosure that have been described as a set or genus, every individual member of the set or genus is intended, individually, as an aspect of the disclosure, even if, for brevity, every individual member has not been specifically mentioned herein. When aspects of the disclosure that are described herein as being selected from a genus, it should be understood that the selection can include mixtures of two or more members of the genus. Similarly, with respect to aspects of the disclosure that have been described as a range, such as a range of values, every subrange within the range is considered an aspect of the disclosure.

DETAILED DESCRIPTION

The disclosure provides compositions and improved methods for delivering skin actives that results in increased efficiency of contact and/or penetration of the skin active with the skin brought about by entrapping or sequestering the skin active within larger order structures formed by self-assembling peptides formed, e.g., on the skin surface. Oligopeptides of 2-20 amino acids that include a structure of alternating hydrophobic and hydrophilic residues and form a self-aggregating peptide are contemplated. These self-assembling peptides allow for the delivery of components from therapeutic or personal care compositions to a subject in need thereof. By entrapping the formulation inside a higher-ordered structure formed by self-assembling polypeptides, even in the presence of a bioactive compound such as a skin active, intimate contact of the skin active with the skin is achieved and prolonged that allows for greater contact and/or penetration over time, resulting in increased efficiency of delivery of the skin active.

DEFINITIONS

The term "amino acid" as employed herein includes and encompasses all of the naturally occurring and synthetic amino acids, either in the D- or L-configuration if optically active.

The term "dermatologically acceptable carrier" as used herein means a carrier that is suitable for topical application to the keratinous tissue. The dermatologically acceptable carrier may be in a wide variety of forms such as, for example, simple solutions (e.g., water-based or oil-based), solid forms (e.g., gels or sticks) and emulsions.

As used herein, the term "peptide" is broad enough to include one or more peptides, one or more derivatives of peptides, and combinations thereof. The term "peptide" means a molecule comprising amino acids covalently linked by peptide bonds as defined herein.

The term "oligopeptide" as used herein refers to a peptide consisting of 2-100, e.g., 2-20 amino acids in length. The term oligopeptide includes peptides such as dipeptides, tripeptides, tetrapeptides, pentapeptides, hexapeptides, heptapeptides, octapeptides, nonapeptides, decapeptides, monodecapeptides, dodecapeptides, tridecapeptides, tetradecapeptides, pentadecapeptides, hexadecapeptides, heptadecapeptides, octadecapeptides, nonadecapeptides and icosapeptides, and their derivatives, including peptide amphiphiles.

All terms such as "skin aging", "signs of skin aging", and the like are used in the sense in which they are generally and widely used in the art of developing, testing and marketing personal care products. "Wrinkles" means furrows in the otherwise smooth surface of the skin, such as the facial skin, visible to the naked eye, generally having an average depth of 50 to more than 200 µm and essentially appearing with progressive age.

In one aspect, described herein is a personal care composition comprising at least one oligopeptide able to self-assemble into a macrostructure, wherein the oligopeptide is 2-100 amino acids in length (e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 amino acids in length), and wherein the oligopeptide has at least one 0- to 10-amino-acid block of hydrophobic amino acids alternating with at least one 1- to 10-amino-acid block of hydrophilic amino acid residues. In some embodiments of the oligopeptide according to the disclosure, if both amino acid blocks are three amino acids or less, there are at least three juxtaposed amino acid blocks (e.g., hydrophilic-hydrophobic-hydrophilic). Other embodiments comprise a personal care composition containing an oligopeptide comprising at least one hydrophilic amino acid block of less than three amino acids alternating with at least one hydrophobic amino acid block, wherein at least one of the hydrophilic or hydrophobic amino acid blocks comprises three amino acids or less. The personal care composition optionally comprises a dermatologically or orally acceptable carrier or injectable liquid as described elsewhere herein. Preferably, the composition comprises an effective amount, preferably a safe and effective amount, of the oligopeptide. For example, in some embodiments, the oligopeptide in the composition is present at a concentration of from about 0.001%, 0.002%, 0.004%, 0.006%, 0.008%, or 0.01% to about 5%, 4%, 2%, 1%, 0.5%, 0.2%, 0.1%, or 0.05% (w/v or v/v) of the composition.

One embodiment of the present invention utilizes self assembled macrostructures of oligopeptides in connection with non-assembled oligopeptide forms or other skin and hair benefit materials to enhance their efficacy by achieving improved, longer lasting delivery and/or penetration.

Skin and hair benefits can be achieved by the oligopeptide macrostructures even in the absence of the biological activity of the non-assembled oligopeptides or even in the absence of other skin and hair actives. Such benefits are achieved by the modification of the surface energy of the substrate, the creation of a barrier layer on the substrate, the modification of the adhesive properties of the substrate, the modification of the optical properties or the surface texture of the substrate and creation and use of macrostructures.

The oligopeptide, in some embodiments, is able to self-assemble into a structure comprising an alpha helix secondary structure. In other embodiments, the oligopeptide is able to self-assemble into a structure comprising a beta-sheet secondary structure. In some embodiments, the oligopeptide exhibits both alpha helix and beta-sheet secondary structures. In some embodiments, the macrostructure consists of the oligopeptides. In still other embodiments, the oligopeptide is able to self-assemble above the critical aggregation concentration into a structure comprising a nanofiber (Aggeli et al.; et al.; *PNAS* 2001, 98, 11857-11862) or below the critical aggregation concentration to adsorb and self-assemble at an interface to create partial up to complete self-assembled monolayers (Whitehouse et al; *Angew. Chem. Int. Ed.* 2005, 44, 1965-1968). Formation of membranes, films or macrofibers by the oligopeptides are specifically contemplated. The process of creating a long macrofiber at the interface of an aqueous solution of a peptide amphiphile and a complementary polymer, has been described previously (Capito et al., Science, 319: 1812, 2008). Alternatively, stable macrofibers could be created by drawing a heat treated peptide amphiphile suspension through a salt solution (Zhang et al., Nat. Mater., 9:594, 2010). In some embodiments, a similar technical approach is applied to extend hair fibers (hair or eyelashes) for improved, customized appearance. Special formulations and/or applicators can be used for this cosmetic method.

The oligopeptide comprises blocks of alternating hydrophobic and hydrophilic amino acid residues. For example, in some embodiments, the hydrophobic amino acid block within the oligopeptide has a length of 1, 2, 3, 4, or 5 amino acids. In some embodiments, the hydrophilic amino acid block within the oligopeptide has a length of 1, 2, 3, 4, or 5 amino acids.

In some embodiments, the hydrophilic amino acid residue is a charged amino acid residue at a physiological pH. Exemplary hydrophilic amino acid residues include, but are not limited to, arginine, lysine, glutamate, aspartate, histidine, threonine, serine, glutamine, asparagine and ornithine. Exemplary hydrophobic residues in the oligopeptide include, but are not limited to, alanine, proline, glycine, tyrosine, tryptophan, phenylalanine, valine, leucine, isoleucine, methionine and cysteine.

The oligopeptide in the composition optionally comprises at least one terminal amino acid that has been modified with a non-amino acid organic functional group. Exemplary non-amino acid organic functional groups include, but are not limited to, an alkyl group, an acyl group, a carbohydrate, a polyether, a phosphate, and a fatty acid. In embodiments where the non-amino acid functional group is a phosphate, the phosphate is optionally farnesyl pyrophosphate, geranyl pyrophosphate or 3-isopentenyl pyrophosphate.

In order to enhance the sub-surface bioavailability, the epithelial barrier-crossing properties of those peptides can be improved by increasing their lipophilicity or lipophilic character either by acylation of the N-terminal $NH_2$ group of the peptide or by esterification of the carboxyl group with an alcohol, linear or branched, saturated or unsaturated, hydroxylated or not, or both. In some embodiments, N-acyl groups used to modify the peptide backbone of an oligopeptide include, but are not limited to, lauroyl ($C_{12}$), myristoyl ($C_{14}$), palmitoyl ($C_{16}$), stearoyl ($C_{18}$), oleoyl ($C_{18:1}$), arachidic ($C_m$) or linoleoyl ($C_{18:2}$) groups. Biotinyl groups (biotin or derivatives) are also contemplated. In some embodiments, the N terminal group is either an H or a palmitoyl group.

In some embodiments, the peptide is a PuraMatrix™ peptide. PuraMatrix™, a modified hexadecapeptide RADARADARADARADA (SEQ ID NO: 1) where R is Arginine, A is Alanine, and D is Aspartic acid), is a synthetic matrix that is used to create defined three-dimensional (3D) micro-environments for a variety of cell culture experiments. It is known to act as a biological active for tissue regeneration. It also forms strong three-dimensional structures that can contain liquids and protect tissues from microbial and mechanical stresses. PuraMatrix™ (an amphoteric oligopeptide) significantly upregulates claudin-1 (CLDN1) when used at concentrations above the estimated critical aggregation concentration. CLDN1 is involved in skin barrier function by coupling keratinocytes to each other in the stratum corneum. Thus, the incorporation of a PuraMatrix™ peptide in skin care formulations provides moisturization benefits. In some embodiments, the PuraMatrix™ peptide creates a strong scaffold providing an effective physical skin moisture barrier, and enables effective and controlled delivery of a variety of other materials or actives by allowing intimate contact of those actives with the epidermis.

Analogs of PuraMatrix™ proteins are also contemplated. Exemplary analogs include, but are not limited to, ARADARADARADARAD (SEQ ID NO: 2), AKADAKADAKADAKAD (SEQ ID NO: 3), AHADAHADAHADAHAD (SEQ ID NO: 4), ARAEARAEARAEARAE (SEQ ID NO: 5), AKAEAKAEAKAEAKAE (SEQ ID NO: 6), and AHAEAHAEAHAEAHAE (SEQ ID NO: 7). See U.S. Patent Application Publication No. 2009/0111734, the disclosure of which is incorporated herein by reference in its entirety. Other contemplated analogs include deleting the alanine residue in any of the sequences described herein and replacing it with a valine, leucine or isoleucine; and/or deleting the arginine residue in any of the sequences described herein and replacing it with a lysine, and/or deleting the aspartic acid residue in any of the sequence described herein and replacing it with a glutamic acid.

In some embodiments, analogs of PuraMatrix™ proteins including proteins which have been modified to comprise non-natural amino acids; D- or L-amino acids; amino acids connected with sulfide bridge bonds, and combinations thereof are contemplated. Combinations of the oligopeptide modifications that demonstrate biological activity with a three dimensional matrix are specifically contemplated (US20090162437A1 and US2012014925A1).

The oligopeptide comprises a block of hydrophobic residues followed by a block of hydrophilic residues. For example, in some embodiments, the oligopeptide comprises an amino acid sequence such as RARADADA (SEQ ID NO: 8), RARARADADADA (SEQ ID NO: 9) or RARARARADADADADA (SEQ ID NO: 10).

In some embodiments, the oligopeptides described in U.S. Pat. Nos. 7,906,478; 7,534,761; 7,554,021; 7,731,719; 7,713,923; 7,745,708; 8,124,583; 7,491,690; 7,838,491; 8,063,014; 6,890,654; 5,670,483; 6,548,630; 6,800,481; 7,098,028; U.S. Patent Application Publication Nos.: US 2005/0272662; US 2007/190603; US 2012/014925; International Application Publication Nos. WO 2012/08967; WO 2008/121447; WO 2008/127256; WO 2008/101104; WO 2007/172757; WO 2006/116524; WO 2005/014615; WO 2003/084980, and Stupp et al., Nat. Mater., 9:594, 2010; Matson et al., Curr. Opin. Solid State Mat. Sci., 15:225-235, 2011; Capito et al., Science, 319:1812, 2008, Kao et al., Tissue Engineering, 15:2385-2396, 2009; Hui Meng et al., J. Biomed. Mat. Res., Part B: Appl. Biomat., 89B:379-391, 2009; Rutledge et al., Nanomedicine, 2:207-215, 2006, the disclosures of which are incorporated herein by reference in their entireties, are incorporated into a personal care composition described herein.

In some embodiments, the composition optionally includes one or more of the oligopeptides disclosed in U.S. Pat. No. 6,492,326, (e.g., pentapeptides such as lys-thr-thr-lys-ser (SEQ ID NO: 13), and derivatives thereof). Suitable pentapeptide derivatives include palmitoyl-lys-thr-thr-lys-ser (SEQ ID NO: 14) (available from Sederma, France). Another optional oligopeptide that can be used in the composition herein is carnosine. In some embodiments, the optionally included peptide is not present in an effective amount (e.g., it is included in the composition for a purpose other than the desired benefits disclosed herein).

In some embodiments, the composition optionally does not comprise a pentapeptide (e.g., palmitoyl-lys-thr-thr-lys-ser (SEQ ID NO: 14)).

The personal care composition described herein optionally further comprises a polymer having a charge opposite to the charge of the oligopeptide, wherein the oligopeptide and the polymer assemble into a macrostructure.

In addition, in most cases, variables such as pH, salt concentration, temperature, and peptide concentration establish conditions that play a central role in the formation of macrostructures. The anticipated important macrostructures for beauty applications are nanofibers, macrofibers, membranes and hydrogels, optionally in combination with the biological activity of the peptides, or part of the peptide. The corresponding benefits include (1) moisturization via the peptide biological activity, (2) physical barrier properties and enhanced penetration of other actives achieved by the formation of a surface membrane structure, (3) skin tightening achieved by stretching of a peptide film, and (4) fiber formation/extension of hair or eyelashes. Additional benefits include, but are not limited to; slow release of the active peptide to provide a constant long-lasting benefit, long-lasting anti-bacterial/anti-fungal layer to prevent odor, acne and dandruff and non-biological routes to grow hair (e.g., for use in chemical hair extensions, mascaras and eyebrow replenishment products).

Various product forms have been reported in the medical field containing RADA-16I (SEQ ID NO: 1), including gels, membranes, powders, sprays, films, liquids, creams, foams, emulsions. These forms are also relevant to beauty applications, as are masks, patches, applicators.

Formulation parameters that affect macrostructure assembly formation include salt and peptide concentration. The self assembling of the oligopeptide before, during, or after application to the substrate may take place because of changes of the pH, triggered by the application of the formulation on the substrate. More specifically, the skin pH (approximate value of 5.5) can contribute a significant change of the formulation pH, allowing oligopeptide self-assembling. Other mechanisms of initiation can include pH, salt concentration, and oligopeptide concentration changes via evaporation of the carrier.

The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to a composition herein. Examples of these ingredient classes include, but are not limited to: abrasives, absorbents, aesthetic components such as fragrances, pigments, colorings/colorants, essential oils, skin sensates, astringents, such as cosmetic and drug astringents (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic biocides, denaturants, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, preservatives, propellants, reducing agents, sebum control agents, and sequestrants.

Other optional components which may be incorporated in a composition described herein include, but are not limited to, one or more cosmetic skin care agents. A cosmetic skin care agent is any substance, material, or compound, intended to be applied to the skin for the purpose of improving an undesirable skin condition (or symptom thereof). Some undesirable skin conditions include outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

Some non-limiting examples of cosmetic skin care agents include, but are not limited to, skin bleaching and lightening agents (e.g., hydroquinone, kojic acid, ascorbic acid, magnesium ascorbyl phosphate, ascorbyl glucoside, pyridoxine), enzymes, coenzymes, skin-conditioning agents (e.g., humectants and occlusive agents) skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), vitamins and derivatives thereof, hydroxy acids, sunscreen agents, chelators, anti-oxidants and radical scavengers, sugar amines (e.g., N-acetylglucosamine), vitamin B3 compounds (e.g., niacinamide), sodium dehydroacetate, dehydroacetic acid and its salts, phytosterols, soy derivatives (e.g., equol and other isoflavones), phytantriol, farnesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole their derivatives, and combinations thereof. Some examples of vitamins include water-soluble vitamins such as vitamin B1, B2, B6, B12, C, pantothenic acid, pantothenyl ethyl ether, panthenol, biotin, and their derivatives, water-soluble amino acids such as asparagine, alanine, indole, glutamic acid and their salts, water-insoluble vitamins such as vitamin A, D, E, and their derivatives, water-insoluble amino acids such as tyrosine, tryptamine (and their salts), and combinations thereof. Some examples of cosmetic skin care agents are also described in U.S. Pat. Nos. 5,652,230; 5,833,998; 6,217,888; 2008/0206373; 2010/0189669; 2010/0239510; 2008/0075798; and 2010/0227011.

Botanicals may be derived from one or more of a root, stem bark, leaf, seed or fruit of a plant. Some botanicals may be extracted from a plant biomass (e.g., root, stem, bark, leaf, etc.) using one more solvents. Botanicals may comprise a complex mixture of compounds and lack a distinct active ingredient.

Other examples of optional ingredients can include cationic polymers, conditioning agents (hydrocarbon oils, fatty esters, silicones), anti-dandruff agents, anti-seborrheic agents, antipsoriasis agents, suspending agents, viscosity modifiers, dyes, nonvolatile solvents or diluents (water soluble and insoluble), pearlescent aids, foam boosters, surfactants, nonionic cosurfactants, pediculocides, pH adjusting agents, perfumes, preservatives, chelants, chelating agents, proteins, UV absorbers, pigments, other amino acids, other vitamins, and combinations thereof.

The compositions described herein optionally further comprise one or more pigment materials. Exemplary pigment materials include, but are not limited to, inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical pigments and natural colors, including, but not limited to, water-soluble components such as those having C. I. Names. The compositions of the present disclosure optionally comprise antimicrobial agents that are useful as cosmetic biocides and anti-dandruff agents, including water-soluble components such as piroctone olamine, water-insoluble components such as 3,4,4'-trichlorocarbanilide (trichlosan), triclocarban and zinc pyrithione.

Personal care compositions for topical use optionally may comprise a dermatologically acceptable carrier. The carrier may thus act as a diluent, dispersant, solvent, or the like for the oligopeptide and other materials, compounds and/or agents. The carrier may contain one or more dermatologically acceptable solid, semi-solid or liquid fillers, diluents, solvents, extenders and the like. The carrier may be solid, semi-solid or liquid. The carrier can itself be inert or it can possess dermatological benefits of its own. Concentrations of the carrier can vary with the carrier selected and the intended concentrations of the essential and optional components.

In one embodiment, the carrier is present at a level of from about 50% to about 99.99% (e.g., from about 60% to about 99.9%, or from about 70% to about 98%, or from about 80% to about 95%), by weight of the composition. The dermatologically acceptable carrier may be provided in a wide variety of forms. Non-limiting examples include, but are not limited to, simple solutions (water or oil-based), emulsions, and solid or semi-solid forms (gels, sticks). For example, emulsion carriers can include, but are not limited to, oil-in-water, water-in-oil, water-in-silicone, water-in-oil-in-water, and oil-in-water-in-silicone emulsions. As will be understood by the skilled artisan, a given component will distribute primarily into either the water or oil phase, depending on the water solubility/dispersability of the component in the composition. In some embodiments, a personal care composition described herein is formulated into an oil-in-water emulsion.

Some preferred carriers contain a dermatologically acceptable, hydrophilic diluents, including water, organic hydrophilic diluents such as lower monovalent alcohols (e.g., C1-C4) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsions contain an aqueous phase and a lipid or oil phase. Lipids and oils are derived from animals, plants, or petroleum and may be natural or synthetic. In some embodiments, the emulsion comprises a humectant, such as glycerin. Emulsions optionally further comprise from about 0.1% to about 10% (or from about 0.2% to about 5%) of an emulsifier, based on the weight of the composition. Emulsifiers may be nonionic, anionic or cationic. Suitable emulsifiers are disclosed in, for example, U.S. Pat. No. 3,755,560, U.S. Pat. Nos. 4,421,769, 6,217,888, and McCutcheon's Detergents and Emulsifiers, North American Edition, pages 317-324 (1986). Suitable emulsions may have a wide range of viscosities, depending on the desired product form.

Suitable carriers also include oils. The personal care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. The oils may be volatile or nonvolatile. "Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable. When the skin care composition is in the form of an emulsion, oils are carriers typically associated with the oil phase.

Suitable oils also include volatile oils. In certain embodiments, the volatile oils may have a viscosity ranging from about 0.5 to 5 centistokes at 25° C. Volatile oils may be used to promote more rapid drying of the skin care composition after it is applied to skin. Nonvolatile oils are also suitable for use in the composition. Nonvolatile oils are often used for emolliency and protective properties.

Suitable silicone oils include polysiloxanes. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the personal care composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The skin care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Some suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

In some embodiments, the personal care compositions described herein are in the form of pourable liquids (under ambient conditions). The compositions can therefore comprise an aqueous carrier, which is typically present at a level of from about 20% to about 95% (or from about 60% to about 85%) based on weight of the composition. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

In embodiments wherein the personal care composition is to be ingested, the composition optionally comprises an orally acceptable carrier. The use of any suitable orally ingestible carrier or carrier form, as known in the art, is contemplated. Non-limiting examples of oral personal care compositions include, but are not limited to, tablets, pills, capsules, drinks, beverages, powders, vitamins, supplements, health bars, candies, chews, and drops.

In some embodiments the personal care composition comprises a liquid that is acceptable for injection in and/or under the skin if the composition is to be injected. Any suitable injectable liquid as known in the art, or otherwise, is contemplated.

The personal care compositions described herein are prepared by conventional methods known in the art for making topical, oral and injectable compositions. Such methods typically involve mixing of the ingredients in one or more steps to a relatively uniform state, with or without heating, cooling, application of vacuum, and the like.

In another aspect, the present disclosure provides a method of regulating mammalian skin comprising administering an effective amount of a personal care composition. In some embodiments, the regulating of mammalian skin comprises treatment of a mammalian keratinous tissue condition. Such treatment of keratinous tissue conditions can include prophylactic and therapeutic regulation, including regulating the cosmetic appearance of the mammalian keratinous tissue. In some embodiments, the regulating a property of mammalian skin includes, but is not limited to, preventing, retarding, and/or treating uneven skin tone; reducing the size of pores in mammalian skin; regulating oily/shiny appearance of mammalian skin; thickening keratinous tissue (i.e., building the epidermis and/or dermis and/or subcutis layers of the skin and where applicable the keratinous layers of the nail and hair shaft); preventing, retarding, and/or treating uneven skin tone by acting as a lightening agent or a pigmentation reduction cosmetic agent; preventing, retarding, and/or treating atrophy of mammalian skin; softening and/or smoothing lips, hair and nails of a mammal; preventing, retarding, and/or treating itch of mammalian skin; preventing, retarding, and/or treating the appearance of dark under-eye circles and/or puffy eyes; preventing, retarding, and/or treating sallowness of mammalian skin; preventing, retarding, and/or treating sagging (i.e., glycation) of mammalian skin; preventing and/or retarding tanning of mammalian skin; desquamating, exfoliating, and/or increasing turnover in mammalian skin; preventing, retarding, and/or treating hyperpigmentation such as post-inflammatory hyperpigmentation; preventing, retarding, and/or treating the appearance of spider vessels and/or red blotches on mammalian skin; preventing, retarding, and/or treating fine lines and wrinkles of mammalian skin; preventing, retarding, and/or treating skin dryness (i.e., roughness, scaling, flaking); and preventing, retarding, and/or treating the appearance of cellulite in mammalian skin. In some embodiments, the composition is used to treat the signs of aging. For example, in some embodiments, the composition is used to regulate the signs of aging. In some embodiments, the composition is used to reduce or decrease the signs of aging. In some embodiments, the composition is used to prevent the signs of aging in keratinous tissue (e.g., skin, hair, or nails).

Regulating keratinous tissue conditions can involve topically applying to the keratinous tissue a safe and effective amount of a composition of the present disclosure. Non-limiting examples of skin care compositions include, but are not limited to, sunscreens and blocks, mousse, bath and shower gels, lip balms, skin conditioners, cold creams, moisturizers, soaps, body scrubs, body wash, face wash, body spray, exfoliants, astringents, scruffing lotion, depilatories shaving, pre-shaving and after-shaving products, deodorants and antiperspirants, cleansers, skin gels, and rinses, skin lightening and self-tanning compositions. Non-limiting examples of hair care compositions include, but are not limited to, shampoo, conditioner, treatment, styling, hair spray, permanent styling, tonics, cream rinse, hair dye, hair coloring, hair bleaching, hair shine, hair serum, anti-frizz, voluminizers, split-end repair, anti-dandruff formulations, and mascara. Non-limiting examples of other personal care compositions include but are not limited to lipstick, rouge, foundation, blush, eyeliner, lip liner, lip gloss, facial or body powder, nail polish, eye shadow, toothpaste, mouth wash, and oral care strips. Furthermore, the composition can be applied topically through the use of a patch or other delivery device. Delivery devices can include, but are not limited to, those that can be heated or cooled, as well as those that utilize iontophoresis or ultrasound.

In some embodiments, for example, the personal care composition described herein is in the form of a skin lotion, clear lotion, milky lotion, cream, gel, foam, ointment, paste, emulsion, spray, conditioner, tonic, cosmetic, lipstick, foundation, nail polish, after-shave, or the like, which is intended to be left on the skin or other keratinous tissue for some aesthetic, prophylactic, therapeutic or other benefit (i.e., a "leave-on" composition or skin care composition). After applying the composition to the keratinous tissue (e.g., skin), it is preferably left on for a period of at least about 15 minutes, more preferably at least about 30 minutes, even more preferably at least about 1 hour, even more preferably for at least several hours, e.g., up to about 12 hours. Any part of the external portion of the face, hair, and/or nails can be treated, (e.g., face, lips, under-eye area, eyelids, scalp, neck, torso, arms, hands, legs, feet, fingernails, toenails, scalp hair, eyelashes, eyebrows, etc.). The application of the present compositions may be done using the palms of the hands and/or fingers or a device or implement (e.g., a cotton ball, swab, pad, applicator pen, spray applicator, etc.).

In some embodiments, for example, the personal care composition described herein is in the form of face wash, body wash, shampoo or hair conditioner, which is intended to be rinsed-off of skin or hair for cleaning, conditioning, therapeutic treatment or other benefit (i.e., a "rinse-off" composition). After applying the composition to the skin or hair, with or without dilution with additional water, the composition is left on for a period of at least about a minute (or at least 2 minutes, at least 3 minutes, at least 4 minutes, at least 5 minutes or longer) before the compositions is rinsed with water to remove the bulk of the composition from the skin or hair. Some examples of body wash compositions suitable for including at least one oligopeptide are described in U.S. Pat. Nos. 6,451,333; 6,335,312; 6,673,755; 2009/0029900; and 2004/0057920.

Another approach to ensure a continuous exposure of the keratinous tissue to at least a minimum level of the composition is to apply the compound by use of a patch applied, e.g., to the face. Such an approach is particularly useful for problem skin areas needing more intensive treatment (e.g., facial crows-feet area, frown lines, under-eye area, upper lip, and the like). The patch can be occlusive, semi-occlusive or non-occlusive, and can be adhesive or non-adhesive. The composition can be contained within the patch or be applied to the skin prior to application of the patch. In some embodiments, the patch is formed from the self assembled peptide structure itself, without the need for an additional, non-peptide substrate. The patch can also include additional actives such as chemical initiators for exothermic reactions such as those described in PCT application WO 9701313, and in U.S. Pat. Nos. 5,821,250, 5,981,547, and 5,972,957. The patch can also contain a source of electrical energy (e.g., a battery) to, for example, increase delivery of the composition and active agents (e.g., iontophoresis). The patch is preferably left on the keratinous tissue for a period of at least about 5 minutes, or at least about 15 minutes, or at least about 30 minutes, or at least about 1 hour, or at night as a form of night therapy.

In some embodiments, a treatment method described herein comprises orally administering a personal care composition described herein to a mammalian subject. Non-limiting examples of oral personal care compositions can include, without limitation, tablets, pills, capsules, drinks, beverages, powders, vitamins, supplements, health bars, candies, chews, and drops.

The amount of the composition that is administered to the subject, the frequency of application, and the period of use will vary widely depending upon the level of components of a given composition and the level of regulation desired, e.g., in view of the level of skin tissue (e.g., keratinous tissue) damage present or expected to occur.

In some embodiments, the personal care compositions described herein are useful for regulating visible and/or tactile discontinuities in mammalian keratinous tissue, including discontinuities in skin texture and color. For example, the apparent diameter of pores can be decreased, the apparent height of tissue immediately proximate to pore openings can approach that of the interadnexal skin; the skin tone/color can become more uniform; and/or the length, depth, and/or other dimension of lines and/or wrinkles can be decreased. Skin smoothing compositions are known in the art and they attempt to reduce the appearance of wrinkle by changing skin texture (smoothen and flatten wrinkles and skin texture imperfections). Exemplary skin smoothing compositions known in the art optionally comprise particles, film formers and adhesives. Drawback of such compositions include visibility of the treatment, skin discomfort, irritation, cracking of the skin coating and incompatibility with other ingredients of the product composition. In contrast, compositions comprising the oligopeptides described herein self-assemble into membranes that provide wrinkle reduction benefits because they possess the following characteristics: optical transparency; conform to the skin, modifying its texture and filling skin wrinkles; contract upon drying; and flexibility, leading to durability of benefit.

In some embodiments, the personal care compositions described herein are useful for cleansing (e.g, hair, body, facial), improving keratinous tissue feel or appearance (wet & dry) such as for hair (e.g., improving appearance/look, detangling, improving shine, gloss, decreasing coefficient of friction, increasing smoothness, retaining color, decreasing split ends, preventing hair breakage, preventing environmental damage such as sunlight damage and treating smoke damage, and damage from pollutants such as nitrogen oxides, sulfur oxides, ozone, and metals such as lead), odor control, oil control, conditioning, hair volume control, hair growth, and hair growth inhibition.

Shampoo compositions may incorporate oligopeptides at a concentration of above or below the critical aggregation concentration. The shampoo formulations may be a solution, an aqueous emulsion or an aqueous microemulsion and further comprise one or more ingredients, including but not limited to detersive surfactants, aqueous carriers, cationic polymers, non-ionic polymers, and conditioning agents. A shampoo composition may comprise from about 5% to about 20% of a detersive surfactant by weight of the shampoo composition. Detersive surfactants may include but are not limited to anionic detersive surfactants, zwitterionic or amphoteric detersive surfactants, and combinations thereof. Some non limiting examples of anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528, 378.

A shampoo composition may comprise an aqueous carrier. A shampoo composition may comprise from about from about 60% to about 85% by weight of the shampoo composition of an aqueous carrier. The aqueous carrier may comprise water, or a miscible mixture of water and organic solvent.

A shampoo composition may comprise one or more cationic polymers that include nitrogen-containing moieties such as quaternary ammonium or cationic protonated amino moieties. Some examples include but are not limited to modified guars, cationic cassia, other synthetic polymers. A variety of non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

A shampoo composition may comprise a non-ionic polymer, such as a polyalkylene glycol, a conditioning agent such as a hydrocarbon oil, fatty ester, or silicone material. Other ingredients which may be optionally incorporated in a shampoo composition include anti dandruff agents, suspending agents, viscosity modifiers, dyes, nonvolatile solvents or diluents, pearlescent aids, foam boosters, additional surfactants or nonionic cosurfactants, pediculocides, pH adjusting agents, perfumes, preservatives, chelants, aminoacids, proteins, skin active agents, sunscreens, UV absorbers, and vitamins.

A hair conditioning composition may incorporate an oligopeptides at a concentration of above or below the critical aggregation concentration. A hair conditioning composition may be provided as an emulsion or microemulsion and further comprise one or more ingredients including but not limited cationic surfactants, fatty compounds, aqueous carrier, and silicone materials.

A hair conditioning composition may comprise a cationic surfactant at a concentration from about 0.5 to about 10% by weight of the hair conditioning composition. Some non-limiting examples include mono- and di-alkyl chain cationic surfactants.

A hair conditioning composition may comprise a fatty compound, such as a fatty alcohol, fatty acid, a fatty alcohol derivative, a fatty acid derivative, and mixtures thereof. A hair conditioning composition may also comprise an aqueous carrier at a concentration from about 80% to about 95% by weight of the hair conditioning composition. The aqueous carrier may be water and water solutions of lower alkyl alcohols and polyhydric alcohols. A hair conditioning composition may comprise a silicone compound or mixture of silicone compounds at a concentration from about 0.2% to about 8% by weight of the hair conditioning composition.

A cationic surfactant, together with a high melting point fatty compounds and an aqueous carrier, may form a gel matrix in the hair conditioning composition, which may provide various hair conditioning benefits such as slippery feel during the application to wet hair and softness and moisturized feel on dry hair.

Additional materials that may be optionally included in a hair conditioning composition include, but are not limited to, cationic polymers, low melting oils, other conditioning agents, vitamins, panthenol and derivatives, hydrolysed keratin, proteins, plant extracts, and nutrients; preservatives, pH adjusting agents, ultraviolet and infrared absorbing agents, anti dandruff agents, suspending agents, viscosity modifiers, dyes, nonvolatile solvents or diluents, pearlescent agents, pediculocides, perfumes, chelants, salts, sunscreens.

In some embodiments, the personal care compositions described herein are useful as anti-perspirant/anti-odorant compositions optionally comprising one or more of the following components in addition to the oligopeptide(s): an antibacterial agent, a perfume, or an odor absorber. The oligopeptide in this case forms a membrane that encompasses the other component(s), bringing them into intimate contact with the skin and allows for durable exposure of the skin to the materials allowing improved effectiveness and duration. In one embodiment in the case of anti-perspirant/anti-odorant, the self assembly of the oligopeptide on the skin can be triggered by the increase of the concentration of the oligopeptide via evaporation of the carrier, the change of the pH by the contact of the composition with skin (typical pH of skin is 5.5), the increase of the salt concentration by the sweating of the consumer or the combination of these.

In some embodiments, the personal care compositions described herein are useful for hair conditioning comprising an oligopeptide(s) and, optionally a conditioning material. The oligopeptide in this case can form a membrane covering the hair fiber and optionally containing conditioning actives. The membrane and the other conditioning materials can modify hair surface characteristics such as surface energy, provide a moisture barrier, texture towards smoothness, optical properties (refractive index), promote a better feel, compatibility/manageability, and improve shine and appearance. In one embodiment in the case of hair care products, the self assembly of the oligopeptide on the hair or scalp can be triggered by the increase of the concentration of the oligopeptide via evaporation of the carrier, the increase of the temperature towards ambient temperature or higher in the case of hair dryer, flat iron, or otherwise. Heating of the composition increases the concentration of the oligopeptide via evaporation and, therefore, favors self-assembly. Additionally, the heat treatment leads to the formation of a liquid crystal phase containing plaque-like sheets that break apart into aligned nanofiber bundles upon cooling, which can be used to create macrofibers when drawn through salt solutions (Zhang, S. et. al.; *Nature Materials* 2010, 9, 594-601).

In some embodiments, the personal care compositions described herein are useful for generating extension of hair fibers (e.g., extending eyelash length and hair extensions). Certain self-assembling peptides are able to aggregate into macrofibers that can be used for this benefit. More specifically, certain peptide amphiphiles form nanofibers under controlled conditions. Macrofibers can be produced by peptide amphiphile suspension and calcium salts. For example a thermally pre-treated solution of an oligopeptide (VVVAAAEEE—SEQ ID NO: 11) modified with an alkyl group (C16 to C22) at the N-terminus can produce strong and flexible macrofibers when brought into contact with a calcium salt solution (Zhang et al.; *Nature Materials,* 2010, 9,594). Alternatively, macrofibers can be drawn from the interface between a solution of peptide amphiphile, even without the heat pretreatment, and a solution of ionic polymer having charge opposite to the charged species of the peptide amphiphile. Specifically, a solution of oligopeptide VVVAAAKKK (SEQ ID NO: 12) modified with an alkyl group (C16) at the N-terminus is placed in one chamber of a two-compartment implement and a solution of a polymer with opposite to the oligopeptide charge is placed in the other chamber (Capito et al., Science, 319: 1812, 2008). A process of contacting the implement with the ends of the hair fiber, and pulling away while co-dispensing the materials creates elongated fibers, i.e. hair or eyelash extensions.

In some embodiments, the composition is chronically applied to the skin or hair, e.g., by topical administration. By "chronic application" is meant continued topical application of the composition over an extended period during the subject's lifetime (e.g., for a period of at least about one week, for a period of at least about one month, for a period of at least about three months, for a period of at least about six months, or for a period of at least about one year). While benefits are obtainable after various maximum periods of use (e.g., five, ten or twenty years), in some embodiments, chronic applications continue throughout the subject's lifetime. Typically, applications would be on the order of about one per day over such extended periods; however, application rates can vary, and can include from about once per week up to about three times per day or more.

A wide range of quantities of the compositions of the present disclosure can be employed to provide a keratinous tissue appearance and/or feel benefit when applied topically.

For example, quantities of the present compositions, which are typically applied per application are, in mg composition/cm² keratinous tissue, from about 0.1 mg/cm² to about 20 mg/cm². A particularly useful application amount is about 0.5 mg/cm² to about 10 mg/cm².

In another aspect, described herein is a personal care regimen utilizing one or more of the personal care compositions described herein for the purpose of regulating the condition of skin or hair. The term "regimen" as used herein refers to the use of a combination of products, at the same or different time. For example, a regimen comprising sequential use of shampoo, conditioner, and styling products, followed by a hair extension application will provide a multiplicity of benefits. Another example of a regimen is the use of an oral composition in conjunction with a topical composition. In some embodiments, the various compositions are packaged together as a kit. In some embodiments, compositions are not packaged together as a kit, but potential users of the regimen are informed (e.g., through advertisements and/or product labeling) that compositions may be used in conjunction with one another to regulate the condition of hair or skin. At least one of the compositions comprises an oligopeptide as described herein. In some embodiments, all compositions comprise an oligopeptide as described herein.

EXAMPLES

Examples 1-5

Moisturizing Oil-in-Water Lotions/Creams

|  | Example | | | | |
|---|---|---|---|---|---|
|  | 1 | 2 | 3 | 4 | 5 |
| Water Phase: | | | | | |
| Water | qs | qs | qs | qs | qs |
| Glycerin | 3 | 5 | 7 | 10 | 15 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2 | 0.5 | — | 3 | 5 |
| Triethanolamine | — | 0.25 | — | — | — |
| D-panthenol | 0.5 | 0.1 | — | 0.5 | 1.5 |
| Sodium Dehydroacetate | 0.5 | 0.1 | 0.5 | 0.1 | 0.5 |
| Benzyl alcohol | 0.25 | 0.25 | 0.25 | 0.25 | 0.25 |
| GLW75CAP-MP (75% aq. TiO2 dispersion)[1] | — | 0.5 | 0.5 | — | — |
| Hexamidine diisethionate | — | 0.1 | — | — | — |
| N-acetyl glucosamine | 2 | 1 | 2 | 2 | 1 |
| Soy Isoflavone | 0.5 | — | — | — | — |
| Oil Phase: | | | | | |
| Salicylic Acid | — | — | 1.5 | — | — |
| Isohexadecane | 3 | 3 | 3 | 4 | 3 |
| PPG15 Stearyl Ether | — | — | 4 | — | — |
| Isopropyl Isostearate | 1 | 0.5 | 1.3 | 1.5 | 1.3 |
| Sucrose polyester | 0.7 | — | 0.7 | 1 | 0.7 |
| Undecylenoyl Phenylalanine | — | 0.5 | — | — | — |
| Phytosterol | — | — | 0.5 | — | 1.0 |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2 | 2.5 | 2 |
| Sodium acrylate/sodium acryloyldimethyl taurate copolymer/isohexadecane/polysorbate 80 | — | 3 | — | — | — |
| Additional Ingredients: | | | | | |
| Dimethicone/dimethiconol | — | 1 | 2 | 0.5 | 2 |
| Polymethylsilsequioxane | — | — | 0.25 | — | 1 |
| Nylon-12 | — | 0.5 | — | — | — |
| Prestige Silk Violet[3] | — | — | — | — | 1 |
| Timiron Splendid Red[4] | — | 1.0 | — | 2 | — |
| Oligopeptides | 0.001%-5% | 0.001%-5% | 0.001%-5% | 0.001%-5% | 0.001%-5% |

[1]Available from Kobo products
[2]Palmitoyl-lysine-threonine available from Sederma
[3]Titanium dioxide coated mica violet interference pigment available from Eckart
[4]Silica and titanium dioxide coated mica red interference pigment available from Rona In a suitable vessel, combine the water-phase ingredients and heat to 75° C. In a separate suitable vessel, combine the oil-phase ingredients and heat to 75° C. Next, add the oil phase to the water phase and mill the resulting emulsion (e.g., with a Tekmar T-25). Then, add the thickener to the emulsion and cool the emulsion to 45° C. while stirring. At 45° C., add the remaining ingredients. Cool the product to 30° C., stir, and pour into suitable containers.

Examples 6-11

Moisturizing Silicone-in-Water Serums/Lotions

| | Example | | | | | |
|---|---|---|---|---|---|---|
| | 6 | 7 | 8 | 9 | 10 | 11 |
| Water Phase: | | | | | | |
| Water | qs | qs | Qs | qs | qs | qs |
| Glycerin | 3 | 5 | 7 | 10 | 15 | 10 |
| Disodium EDTA | 0.1 | 0.1 | 0.05 | 0.1 | 0.1 | 0.1 |
| Niacinamide | 2 | 0.5 | — | 3 | 5 | 3 |
| Sodium Dehydroacetate | 0.5 | 0.1 | — | 0.1 | 0.5 | 0.1 |
| D-panthenol | 0.5 | 0.1 | — | 0.5 | 1.5 | 0.5 |
| GLW75CAP-MP (75% aq. TiO2 dispersion)[1] | — | 0.4 | — | — | — | 0.4 |
| Ascorbyl Glucoside | — | — | — | — | — | 1 |
| Palmitoyl dipeptide[2] | 0.00055 | 0.00055 | 0.00055 | 0.00055 | 0.00055 | 0.00055 |
| Soy Isoflavone | — | 1 | — | — | — | — |
| N-acetyl glucosamine | 2 | — | 2 | — | 5 | — |
| Silicone/Oil Phase: | | | | | | |
| Cyclomethicone D5 | 10 | 5 | 5 | 10 | 7.5 | 10 |
| Dow Corning 9040 Silicone elastomer[3] | — | 10 | 5 | 5 | 7.5 | 5 |
| KSG-15AP silicone Elastomer[4] | 5 | — | 5 | 5 | 7.5 | 5 |
| Dimethione/dimethiconol | — | 2 | 2 | 1 | 2 | 1 |
| Dimethicone 50 csk | 1 | — | — | — | — | — |
| Salicylic Acid | — | — | 1.5 | — | — | — |
| Phytosterol | — | — | — | 1.0 | — | 0.1 |
| PPG-15 Stearyl Ether | — | — | 4 | 4 | — | — |
| Dehydroacetic acid | — | — | 0.5 | — | — | — |
| Undecylenoyl Phenylalanine | — | — | 0.5 | — | — | — |
| BHT | — | 0.5 | — | — | — | — |
| Vitamin E Acetate | — | 0.5 | 0.1 | 0.1 | — | 0.1 |
| Thickener: | | | | | | |
| Polyacrylamide/C13-C14 isoparaffin/laureth-7 | 2.5 | 2.5 | — | — | — | 3 |
| Sodium acrylate/sodium acryloyl dimethyl taurate copolymer/isohexadecane/polysorbate 80 | — | — | — | 3 | — | — |
| Acrylates/C10-30 alkyl acrylates crosspolymer | — | — | 0.6 | — | 0.5 | — |
| Undecylenoyl Phenylalanine Premix | | | | | | |
| Undecylenoyl Phenylalanine | — | — | — | — | 1 | — |
| Water | — | — | — | — | 24 | — |
| Triethanolamine | — | — | — | — | 0.5 | — |
| Dipalmitoyl Hydroxy-Proline Premix: | | | | | | |
| Water | — | — | — | — | — | 4.4 |
| Triethanolamine | — | — | — | — | — | 0.1 |
| Dipalmitoylhyroxyproline | — | — | — | — | — | 1.0 |
| Additional Ingredients: | | | | | | |
| Triethanolamine | — | — | — | — | 0.6 | — |
| Polymethylsilsequioxane | 0.5 | 0.5 | 1.0 | 1 | 1 | 0.5 |
| Polyethylene | — | 0.5 | 0.5 | 1.0 | — | — |
| Flamenco Summit Green G30D[5] | — | — | 1.0 | — | — | — |
| Silica | — | — | 1 | 0.5 | — | — |

-continued

| | Example | | | | | |
|---|---|---|---|---|---|---|
| | 6 | 7 | 8 | 9 | 10 | 11 |
| Prestige Silk Red[6] | — | — | — | 1.0 | 1.0 | 1.0 |
| Oligopeptides | 0.001%-5% | 0.001%-5% | 0.001%-5% | 0.001%-5% | 0.001%-5% | 0.001%-5% |

[1]GLW75CAP-MP, 75% aqueous titanium dioxide dispersion from Kobo
[2]Palmitoyl-lysine-threonine available from Sederma
[3]A silicone elastomer dispersion from Dow Corning Corp
[4]A silicone elastomer dispersion from Shin Etsu,
[5]Titanium dioxide and tin oxide coated mica green interference pigment from Engelhard
[6]Titanium dioxide coated mica red interference pigment from Eckart In a suitable vessel, combine the water-phase ingredients and mix until uniform. In a separate suitable container, combine the silicone/oil phase ingredients and mix until uniform. Separately, prepare a dipalmitoyl hydroxyproline premix and/or undecylenoyl phenylalanine premix by combining the premix ingredients in a suitable container, heat to about 70° C. while stirring, and cool to room temperature while stirring. Add half the thickener and then the silicone/oil phase to the water phase and mill the resulting emulsion (e.g., with a Tekmar T-25). Add the remainder of the thickener, the dipalmitoyl hydroxyproline premix and/or undecylenoyl phenylalanine premix, and then the remaining ingredients to the emulsion while stirring. Once the composition is uniform, pour the product into suitable containers.

Examples 12-17

Moisturizing Water-in-Silicone Creams/Lotions

| | Example | | | | | |
|---|---|---|---|---|---|---|
| | 12 | 13 | 14 | 15 | 16 | 17 |
| Phase A | | | | | | |
| Water | qs | qs | qs | qs | qs | qs |
| Allantoin | 0.2 | 0.2 | 0.2 | 0.2 | 0.2 | 0.2 |
| disodium EDTA | 0.1 | 0.1 | 0.1 | 0.1 | 0.1 | 0.1 |
| ethyl paraben | 0.2 | 0.2 | 0.2 | 0.2 | 0.2 | 0.2 |
| propyl paraben | 0.1 | 0.1 | 0.1 | 0.1 | 0.1 | 0.1 |
| Caffeine | — | 1 | — | — | — | 1 |
| BHT | — | 0.1 | — | 0.015 | — | — |
| Dexpanthenol | 1 | 0.5 | 1 | 1 | 1 | 1 |
| Glycerin | 7.5 | 10 | 15 | 7.5 | 5 | 15 |
| hexamidine isethionate | — | — | 0.1 | 0.5 | — | — |
| Niacinamide | 2 | — | — | 2 | 3.5 | 5 |
| Palmitoyl-dipeptide[1] | 0.00055 | 0.00055 | 0.00055 | 0.00055 | 0.00055 | 0.00055 |
| Phenylbenzimidazole sulfonic acid | — | — | — | — | 1 | — |
| Sodium Dehydroacetate | 0.5 | — | — | 0.1 | 0.5 | 0.5 |
| benzyl alcohol | 0.25 | 0.25 | 0.25 | 0.25 | 0.25 | 0.25 |
| Triethanolamine | — | — | — | — | 0.6 | — |
| green tea extract | 1 | 1 | 1 | 1 | 1 | 1 |
| Soy Isoflavone | — | 0.5 | — | — | — | — |
| N-acetyl glucosamine | 5 | — | 2 | 5 | 2 | — |
| Sodium metabisulfite | 0.1 | 0.1 | 0.1 | 0.1 | 0.1 | 0.1 |
| Phase B | | | | | | |
| Cyclopentasiloxane | 15 | 15 | 18 | 15 | 15 | 18 |
| Titanium dioxide | 0.5 | 0.5 | 0.75 | 0.5 | 0.5 | 0.75 |
| Phase C | | | | | | |
| C12-C15 alkyl benzoate | — | — | — | 1.5 | 1.5 | — |
| Vitamin E acetate | 0.5 | — | 1 | 0.5 | 0.5 | 1 |
| retinyl propionate | 0.3 | — | — | 0.2 | 0.2 | — |
| Undecylenoyl Phenylalanine | — | — | 0.5 | — | — | — |
| Dipalmitoyl hydroxyproline | — | 1 | — | — | — | — |
| Salicylic Acid | — | 1.5 | 1.5 | — | — | — |
| PPG-15 Stearyl Ether | 4 | 4 | 4 | — | — | — |
| Dehydroacetic Acid | — | 0.5 | 0.1 | — | — | — |
| Phytosterol | 1 | 0.5 | — | — | — | — |
| Phase D | | | | | | |
| KSG-21 silicone elastomer[2] | 4 | 4 | 5 | 4 | 4 | 5 |

-continued

|  | Example | | | | | |
|---|---|---|---|---|---|---|
|  | 12 | 13 | 14 | 15 | 16 | 17 |
| Dow Corning 9040 silicone elastomer[3] | 15 | 15 | 12 | 15 | 15 | 12 |
| Abil EM-97 Dimethicone Copolyol[4] | 0.5 | — | — | 0.5 | 0.5 | — |
| Polymethylsilsesquioxane | 2.5 | 2.5 | 2 | 2.5 | 2.5 | 2 |
| Undecylenoyl Phenylalanine Premix | | | | | | |
| Undecylenoyl Phenylalanine | — | — | — | — | 1 | — |
| Water | — | — | — | — | 24 | — |
| Triethanolamine | — | — | — | — | 0.5 | — |
| Phase E | | | | | | |
| Water | 8.8 | — | — | — | — | 8.85 |
| Triethanolamine | 0.2 | — | — | — | — | 0.25 |
| Dipalmitoylhyroxyproline | 0.5 | — | — | — | — | 1 |
| Oligopeptides | 0.001%-5% | 0.001%-5% | 0.001%-5% | 0.001%-5% | 0.001%-5% | 0.001%-5% |

[1]Palmitoyl-lysine-threonine available from Sederma
[2]KSG-21 is an emulsifying silicone elastomer available from Shin Etsu
[3]A silicone elastomer dispersion from Dow Corning Corp
[4]Abil EM-97 available from Goldschmidt Chemical Corporation In a suitable vessel, blend the Phase A components together using a suitable mixer (e.g., Tekmar model RW20DZM) and mix until all of the components are dissolved. Then, blend the Phase B components together in a suitable vessel and mill using a suitable mill (e.g., Tekmar RW-20) for about 5 minutes. Add the Phase C components to the Phase B mixture with mixing. Then, add the Phase D components to the mixture of Phases B and C and then mix the resulting combination of Phase B, C and D components using a suitable mixer (e.g., Tekmar RW-20) for about 1 hour. If applicable, prepare the undecylenoyl phenylalanine premix and/or Phase E by combining all ingredients, heating the ingredients to 70° C. while stirring, and cooling back to room temperature while stirring. Add the undecylenoyl phenylalanine premix and/or Phase E to Phase A while mixing. Next, slowly add Phase A to the mixture of Phases B, C and D with mixing. Mix the resulting mixture continually until the product is uniform. Mill the resulting product for about 5 minutes using an appropriate mill (e.g., Tekmar T-25).

Examples 18-22

Oil-in-Water Mousse

|  | Example | | | | |
|---|---|---|---|---|---|
|  | 18 | 19 | 20 | 21 | 22 |
| Water Phase: | | | | | |
| Water | qs | qs | qs | qs | qs |
| Glycerin | 3 | 5 | 7 | 10 | 15 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2 | 0.5 | — | 3 | 5 |
| Triethanolamine | — | 0.25 | — | — | — |
| D-panthenol | 0.5 | 0.1 | — | 0.5 | 1.5 |
| Sodium Dehydroacetate | 0.5 | 0.1 | 0.5 | 0.1 | 0.5 |
| Benzyl alcohol | 0.25 | 0.25 | 0.25 | 0.25 | 0.25 |
| GLW75CAP-MP (75% aq. TiO2 dispersion)[1] | — | 0.5 | 0.5 | — | — |
| Undecylenoyl Phenylalanine | 1 | — | 0.5 | — | — |
| Hexamidine diisethionate | — | 0.1 | — | — | — |
| Palmitoyl-dipeptide[2] | 0.00055 | 0.00055 | 0.0001 | 0.00055 | 0.00055 |
| N-acetyl glucosamine | 2 | 1 | 2 | 2 | 1 |
| Soy Isoflavone | 0.5 | — | — | — | — |
| Oil Phase: | | | | | |
| Salicylic Acid | — | — | 1.5 | — | — |
| Isohexadecane | 3 | 3 | 3 | 4 | 3 |
| PPG15 Stearyl Ether | — | — | 4 | — | — |
| Isopropyl Isostearate | 1 | 0.5 | 1.3 | 1.5 | 1.3 |
| Sucrose polyester | 0.7 | — | 0.7 | 1 | 0.7 |
| Undecylenoyl Phenylalanine | — | 0.5 | — | — | — |
| Dipalmitoylhyroxyproline | — | — | — | 1.0 | — |
| Phytosterol | — | — | 0.5 | — | 1.0 |

-continued

|  | Example | | | | |
|---|---|---|---|---|---|
|  | 18 | 19 | 20 | 21 | 22 |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2 | 2.5 | 2 |
| Sodium acrylate/sodium acryloyldimethyl taurate copolymer/isohexadecane/polysorbate 80 | — | 3 | — | — | — |
| Additional Ingredients: | | | | | |
| Dimethicone/dimethiconol | — | 1 | 2 | 0.5 | 2 |
| Polymethylsilsequioxane | — | — | 0.25 | — | 1 |
| Nylon-12 | — | 0.5 | — | — | — |
| Prestige Silk Violet[3] | — | — | — | — | 1 |
| Timiron Splendid Red[4] | — | 1.0 | — | 2 | — |
| Propellant Phase | | | | | |
| 152 A HFC Propellant | 3 | 4 | 2 | 3 | 2 |
| A-70 Propellant | 3 | 2 | 4 | 3 | 4 |
| Oligopeptides | 0.001%-5% | 0.001%-5% | 0.001%-5% | 0.001%-5% | 0.001%-5% |

[1]Available from Kobo products
[2]Palmitoyl-lysine-threonine available from Sederma
[3]Titanium dioxide coated mica violet interference pigment available from Eckart
[4]Silica and titanium dioxide coated mica red interference pigment available from Rona In a suitable vessel, combine the water-phase ingredients and heat to 75° C. In a separate suitable vessel, combine the oil-phase ingredients and heat to 75° C. Next, add the oil phase to the water phase and mill the resulting emulsion (e.g., with a Tekmar T-25). Add the thickener to the emulsion and cool the emulsion to 45° C. while stirring. At 45° C., add the remaining ingredients. Cool the product with stirring to 30° C. and pour into suitable containers. Add propellant and product to a suitable aerosol container, and seal the container.

Examples 23-28

Silicone-in-Water Mousse

|  | Example | | | | | |
|---|---|---|---|---|---|---|
|  | 23 | 24 | 25 | 26 | 27 | 28 |
| Water Phase: | | | | | | |
| Water | qs | qs | qs | qs | qs | qs |
| Glycerin | 3 | 5 | 7 | 10 | 15 | 10 |
| Disodium EDTA | 0.1 | 0.1 | 0.05 | 0.1 | 0.1 | 0.1 |
| Niacinamide | 2 | 0.5 | — | 3 | 5 | 3 |
| Sodium Dehydroacetate | 0.5 | 0.1 | — | 0.1 | 0.5 | 0.1 |
| D-panthenol | 0.5 | 0.1 | — | 0.5 | 1.5 | 0.5 |
| GLW75CAP-MP (75% aq. TiO2 dispersion)[1] | — | 0.4 | — | — | — | 0.4 |
| Ascorbyl Glucoside | — | — | — | — | — | 1 |
| Palmitoyl dipeptide[2] | 0.00055 | 0.00055 | 0.00055 | 0.00055 | 0.00055 | 0.00055 |
| Soy Isoflavone | — | 1 | — | — | — | — |
| N-acetyl glucosamine | 2 | — | 2 | — | 5 | — |
| Silicone/Oil Phase: | | | | | | |
| Cyclomethicone D5 | 10 | 5 | 5 | 10 | 7.5 | 10 |
| Dow Corning 9040 Silicone elastomer[3] | — | 10 | 5 | 5 | 7.5 | 5 |
| KSG-15AP silicone Elastomer[4] | 5 | — | 5 | 5 | 7.5 | 5 |
| Dimethione/Dimethiconol | — | 2 | 2 | 1 | 2 | 1 |
| Dimethicone 50 csk | 1 | — | — | — | — | — |
| Salicylic Acid | — | — | 1.5 | — | — | — |
| Phytosterol | — | — | — | 1.0 | — | 0.1 |
| PPG-15 Stearyl Ether | — | — | 4 | 4 | — | — |
| Dehydroacetic acid | — | — | 0.5 | — | — | — |

-continued

|  | Example | | | | | |
| --- | --- | --- | --- | --- | --- | --- |
|  | 23 | 24 | 25 | 26 | 27 | 28 |
| Undecylenoyl Phenylalanine | — | — | 0.5 | — | — | — |
| BHT | — | 0.5 | — | — | — | — |
| Vitamin E Acetate | — | 0.5 | 0.1 | 0.1 | — | 0.1 |
| Thickener: | | | | | | |
| Polyacrylamide/C13-14 isoparaffin/laureth-7 | 2.5 | 2.5 | — | — | — | 3 |
| Sodium acrylate/Sodium acryloyl-dimethyl taurate copolymer/isohexadecane/polysorbate 80 | — | — | — | 3 | — | — |
| Acrylates/C10-30 alkyl acrylates crosspolymer | — | — | 0.6 | — | 0.5 | — |
| Undecylenoyl Phenylalanine/Dipalmitoyl Hydroxyproline Premix | | | | | | |
| Undecylenoyl Phenylalanine | — | — | — | — | 1 | — |
| Water | — | — | — | — | 24 | 9 |
| Triethanolamine | — | — | — | — | 0.5 | 0.2 |
| Dipalmitoylhyroxyproline | — | — | — | — | — | 1.0 |
| Additional Ingredients: | | | | | | |
| Triethanolamine | — | — | — | — | 0.6 | — |
| Polymethyl Silsequioxane | 0.5 | 0.5 | 1.0 | 1 | 1 | 0.5 |
| Polyethylene | — | 0.5 | 0.5 | 1.0 | — | — |
| Flamenco Summit Green G30D[5] | — | — | 1.0 | — | — | — |
| Silica | — | — | 1 | 0.5 | — | — |
| Prestige Silk Red[6] | — | — | — | 1.0 | 1.0 | 1.0 |
| Propellant Phase | | | | | | |
| 152A HFCPropellant | 3 | 2 | 4 | 1 | 5 | 3 |
| A-70 Propellant | 3 | 4 | 2 | 5 | 1 | 3 |
| Oligopeptides | 0.001%-5% | 0.001%-5% | 0.001%-5% | 0.001%-5% | 0.001%-5% | 0.001%-5% |

[1]GLW75CAP-MP, 75% aqueous titanium dioxide dispersion from Kobo
[2]Palmitoyl-lysine-threonine available from Sederma
[3]A silicone elastomer dispersion from Dow Corning Corp
[4]A silicone elastomer dispersion from Shin Etsu,
[5]Titanium dioxide and tin oxide coated mica green interference pigment from Engelhard
[6]Titanium dioxide coated mica red interference pigment from Eckart In a suitable vessel, combine the water-phase ingredients and mix until uniform. In a separate suitable container, combine the silicone/oil-phase ingredients and mix until uniform. Separately, prepare the undecylenoyl phenylalanine and/or dipalmitoyl hydroxyproline premix by combining the premix ingredients in a suitable container, heat to about 70° C. while stirring, and cool to room temperature while stirring. Add half the thickener and then the silicone/oil phase to the water phase and mill the resulting emulsion (e.g., with a Tekmar T-25). Add the remainder of the thickener, the undecylenoyl phenylalanine and/or dipalmitoyl hydroxyproline premix, and then the remaining ingredients to the emulsion while stirring. Once the composition is uniform, pour the product into suitable containers. Add the product and propellant into an aerosol container. Seal the aerosol container.

Examples 29-31

Shampoo Composition

|  | EXAMPLE | | |
| --- | --- | --- | --- |
| Ingredient | 29 | 30 | 31 |
| Water | q.s. | q.s. | q.s. |
| Polyquaternium 76[1] | 2.50 | — | — |
| Guar, Hydroxylpropyl Trimonium Chloride[2] | — | 0.25 | — |
| Polyquaterium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Silicone[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |

-continued

| Ingredient | EXAMPLE | | |
|---|---|---|---|
| | 29 | 30 | 31 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Preservatives, pH adjusters | Up to 1% | Up to 1% | Up to 1% |
| Oligopeptides | 0.001%-5% | 0.001%-5% | 0.001%-5% |

[1]Mirapol AT-1, Copolymer of Acrylamide(AM) and TRIQUAT, MW = 1,000,000; CD = 1.6 meq./gram; 10% active; Supplier Rhodia
[2]Jaguar C500, MW - 500,000, CD = 0.7, supplier Rhodia
[3]Mirapol 100S, 31.5% active, supplier Rhodia
[4]Sodium Laureth Sulfate, 28% active, supplier: P&G
[5]Sodium Lauryl Sulfate, 29% active supplier: P&G
[6]Glycidol Silicone VC2231-193C
[7]Tegobetaine F-B, 30% active supplier: Goldschmidt Chemicals
[8]Monamid CMA, 85% active, supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

Examples 32-33

Shampoo Composition

| | EXAMPLE | |
|---|---|---|
| | 32 | 33 |
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Citric Acid/Sodium Citrate Dihydrate | pH QS | pH QS |
| Sodium Chloride/Ammonium Xylene Sulfonate | Visc. QS | Visc. QS |
| Water | QS | QS |
| Oligopeptides | 0.001%-5% | 0.001%-5% |

(1) Jaguar C17 available from Rhodia
(2) N-Hance 3269 (with Mol. Wt. of about 500,000 and 0.8 meq/g) available from Aqualon/Hercules
(3) Viscasil 330M available from General Electric Silicones
(4) Gel Networks; See Composition below. The water is heated to about 74*C and the Cetyl Alcohol, Stearyl Alcohol, and the SLES Surfactant are added to it. After incorporation, this mixture is passed through a heat exchanger where it is cooled to about 35*C. As a result of this cooling step, the Fatty Alcohols and surfactant crystallized to form a crystalline gel network.

Gel Network:

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 34

Rinse-Off Conditioner Composition

| | |
|---|---|
| Stearamidopropyldimethylamine | 2.00% |
| L-Glutamic acid | 0.64% |
| Cetyl alcohol | 6.00% |
| Stearyl alcohol | 4.00% |
| Dimethicone/cyclomethicone mixture | 3.00% |
| Kathon CG | 0.03% |
| Benzyl alcohol | 0.50% |
| Methyl paraben | 0.20% |
| Propyl paraben | 0.10% |
| Disodium EDTA | 0.13% |
| Perfume | 0.50% |
| Water | 82.90% |
| Oligopeptides | 0.001-5% |

Example 35

Styling Mousse

The mousse has the following composition in weight percent: 72.73% water; 2.0% Luviskol® VA 73W (50% PVP/VA copolymer available from BASF); 10.0% Carbowax® 600 (PEG-12 available from Dow); 2.0% cyclopentasiloxane (SF1202 available from Momentive); 2.0% silicone emulsion (50% dimethicone emulsion available from Toray Silicones); 0.45% isosteareth-20; 0.50% benzyl alcohol; 0.2% methyl paraben; 0.12% disodium EDTA; 10.0% Propellant Aeron® A-70 (propane/isobutene available from Diversified CPC); and 0.0001%4% oligopeptides.

The mousse is prepared by mixing all the ingredients, except the propellant, into a uniform mixture using a Silverson® L4RT homogenizer (5000 rpm) at 48-52° C. The mixture is then cooled to 25° C., filled into an aerosol container, and the aerosol propellant is added.

Example 36

Mascara Oil-in-Water Formula 1

| MASCARA OIL-IN-WATER FORMULA 1 | % by wt |
|---|---|
| Oligopeptides | 0.001%-5% |
| Vinylacetate/vinyl pyrrolidone copolymer (W735 from International Specialty Products) | 38.0 |
| Deionized water | |
| Paraffin wax | 7.0 |
| Stearic acid | 9.0 |
| Triethanolamine | 1.5 |
| Iron oxide black | 8.5 |
| Ammonium acrylates copolymer emulsion (Sytran 5170, containing 41% by weight water insoluble polymer solids, available from Interpolymer Corp) | 10.0 |

Example 37

Mascara Oil-in-Water Formula 2

| MASCARA OIL-IN-WATER FORMULA 2 | % by wt |
|---|---|
| Oligopeptides | 0.001%-5% |
| Copolymer of vinyl alcohol and poly(oxyalkylene)acrylate ((Vinex, available from Air Products and Chemicals, incorporated via a 1 6.22 w/w % stock solution in deionized water) | 38.19 |
| Deionized water | |

-continued

| MASCARA OIL-IN-WATER FORMULA 2 | % by wt |
|---|---|
| Hectorite (Bentone EW available from Elementis Specialties) | 3.1 |
| Carnauba wax | 1.6 |
| Paraffin wax | 5.9 |
| Beeswax | 3 |
| Stearic acid | 2.1 |
| Triethanolamine | 0.7 |
| Petroleum distillate | 4 |
| Tall oil glycerides (Zonester 85 available from Arizona Chemical Co) | 2 |
| Pentaerythrityl-hydrogenated rosinate (Foral 105 available from Hercules Inc) | 2 |
| Iron oxide black | 10 |
| Ammonium acrylates copolymer emulsion (Syntran 5170, containing 41% by weight water-insoluble polymer solids, available from Interpolymer Corp) | 12.68 |
| Propylene glycol | 1.4 |
| Glycerine | 0.5 |
| Panthenol | 0.28 |
| Preservatives | |

Example 38

RADA Peptides Upregulated CLAUDIN 1 Expression in Keratinocytes

Cultures of human keratinocytes are treated with two concentrations of solutions, of the hexadecapeptide PuraMatrix™ (supplied by BD Science). The lower concentration, which is below the estimated critical aggregation concentration (CAC) at which the RADA-16I (SEQ ID NO:1) monomer self-assembles, while the higher concentration is above the CAC. The results show that the higher concentration solution significantly upregulates CLAUDIN 1, a tight junction protein that improves skin barrier function by improving keratinocyte connections to other keratinocytes.

| KERATINOCYTE EVALUATION OF RADA-16I | CLDN1 LEVEL |
|---|---|
| PuraMatrix ™ Low Concentration | 1.09 |
| PuraMatrix ™ High Concentration | 1.39 |

Based on the data, the oligopeptides described herein are expected to show a moisturization benefit, e.g., as evidenced by improvement of skin barrier properties.

Example 39

Personal Care Composition for Use in Wrinkle Reduction

Contraction Assay Experiments and Results

Materials: Pura Matrix is a hexadecapeptide marketed by BD Science for use in cell cultures. The skin smoothing composition is prepared by heating a 1 ml of PuraMatrix for 30 minutes at 80° C. and cooled over 30 minutes to room temperature.

To measure "contraction", as used herein, one measures the distance in inches (in) between two ends of a foam substrate after treatment with a skin smoothing composition. The foam substrate is a 3 mm thick open-cell polyurethane commercially available from Filtrona Porous Technologies as Medisponge 50 PW (the low strain or Young's modulus of this foam is 38.248 kPa) cut to 1×4 cm. In a 70° C.+/−2° C., 40%+/−2% relative humidity environment, with the foam substrate on a Teflon coated surface, coated also with 0.15 ml of a salt solution (160 mM NaCl and 5.7 mM $CaCl_2$). Then, 150 µL of the skin smoothing composition is dotted evenly atop the substrate, then lightly (~30 g pressure) spread across the substrate to cover the entire surface. The treated substrate is then allowed to dry 24 hours in this constant temperature/humidity environment. Then the distance between the ends of the foam substrate is measured with a ruler. Note: a smaller contraction distance between the ends of the foam substrate indicates greater contraction.

Results indicate that a contraction is observed in the case of hexadecapeptide treatment.

| Initial length of the foam | 40 mm |
|---|---|
| Length after the treatment | 34 mm |

Example 40

Hair Extensions Composition

A peptide VVVAAAEEE (SEQ ID NO: 11) modified with an alkyl group (C16) at the N-terminus is dissolved in water. The 1% solution (by weight) is heated to 80° C., kept at this temperature for 30 minutes and then cooled to 25° C. The resulting gel is placed in one chamber of a two-compartment implement. In the other chamber is placed an aqueous solution of 160 mM NaCl and 10 mM of $CaCl_2$. The implement dispenses the two solutions as it is drawn across the tips of the hair or eyelashes, similar to a mascara product. This creates a oligopeptide macrofiber extension to the natural hair fiber. Optionally, dyes or pigments are incorporated to create the desirable color.

Example 41

Another Hair Extension Composition

A peptide VVVAAAKKK (SEQ ID NO: 12) modified with an alkyl group (C16) at the N-terminus is dissolved in water. The 1% solution (by weight) is placed in one chamber of a two-compartment implement. In the other chamber is placed an aqueous solution of 1% of hyaluronic acid. The implement dispenses the two solutions as it is drawn across the tips of the hair or eyelashes, similar to a mascara product. This creates a oligopeptide macrofiber extension to the natural hair fiber. Optionally, dyes or pigments are incorporated to create the desirable color.

Example 42

Deodorant Example

| Ingredient | % by wt |
|---|---|
| Dipropylene glycol | 20.00 |
| 50% Aqueous aluminum chlorohydrate | 40.00 |
| C20-C40 alcohol[1] | 2.00 |
| C20-C40 pareth 40[2] | 1.00 |
| Petrolatum | 1.75 |
| Fragrance | 1.00 |
| Oligopeptide | 0.001-5% |
| Water | Balance to a total of 100% |

[1] Available from New Phase Technologies as Performachol 350
[2] Available from New Phase Technologies as Performachol 480

Process of making the deodorant can be found in U.S. Patent Application Publication No. 2009/0010972A1. The oligopeptide solution is added along with the dipropylene glycol.

Example 43

Hair Conditioner Example

A conditioner formulation containing the following ingredients is prepared.

| Ingredient | Concentration (% by wt) |
| --- | --- |
| Dow Corning Fluid 345 | 7.00 |
| Polyvinyl isobutyl ether (Lutonal IC 115 supplied by BASF) | 0.02 |
| Corn Starch powder (supplied by CPC International) | 3.50 |
| Stearyl benzyl dimethyl ammonium chloride | 0.30 |
| Ethanol | 7.00 |
| Oligopeptide (RADA type or related sequence) | 0.001-5% |
| Deionized water | Balance to a total of 100% |

Preparation Process

This conditioner is prepared by dissolving 35.0 g of the starch powder in 822 g of deionized water with a high speed mixer (Silverson® L4RT) using a rotor-stator adaptor at 300 rpm at elevated temperature (65° C.) for 60 minutes. Then 3.0 g of the stearyl benzyl dimethyl ammonium chloride are added followed by a solution of 0.2 g Lutonal. IC 115 in 70 g of Dow Corning fluid 345. The speed of the mixer in increased to 1000 rpm and the mixture is sheared until particle size is decreased below 10 micrometers. Then, 70 g of ethanol are added. The mixture is finally cooled to room temperature and then the oligopeptide is added and stirred to dissolve.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, U.S. Provisional Application Ser. No. 61/720,264 is incorporated herein by reference in its entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of using a skin or hair care composition, comprising:
(a) topically applying at least one skin or hair care composition to a skin or hair surface in need of treatment, the at least one skin or hair care composition comprising a dermatologically acceptable carrier and at least one oligopeptide capable of self-assembling into nanofibers or macrostructures, wherein the oligopeptide (i) is from 2 to 20 amino acids in length, (ii) has at least one 1- to 10-amino acid block of hydrophobic amino acid residues alternating with at least one 1- to 10-amino acid block of hydrophilic amino acid residues and (iii) self assembles into nanofibers or macrostructures on the skin or hair surface; and (b) topically applying a second skin or hair care composition to the skin or hair surface, the second skin or hair care composition comprising a polymer of charge opposite to the charge of the oligopeptide of the skin or hair care composition wherein the oligopeptide and polymer of opposite charge leads to nanofibers or macrostructures on the skin or hair surface.

2. The method according to claim 1, wherein the at least one hair or skin care composition further comprises at least one hair or skin care agent.

3. The method according to claim 1, wherein the self assembly is initiated by one of evaporation of at least a portion of the at least one skin or hair care composition, a change in pH of the at least one skin or hair care composition, a temperature change of the at least one skin or hair care composition, and a change in the salt concentration of the at least one skin or hair care composition.

4. The method according to claim 1, wherein the concentration of the oligopeptide is from about 0.001% to 1% by weight of the skin or hair care composition.

5. The method according to claim 2, wherein the skin or hair care agent is selected from the group consisting of vitamin compounds, botanicals, skin lightening agents, humectants, moisturizers, conditioners, hydroxy acids, sunscreen agents, chelators, anti-oxidants, radical scavengers, surfactants, anti-dandruff actives, anti-microbial actives, hair growth actives, niacinamide, caffeine, voluminizers, styling polymers, colorants, pearlescent agents, perfumes, malodor absorbers, preservatives, suspending agents, viscosity modifiers, solvents, diluents, pH adjusters, buffers, salts, deposition polymers and mixtures thereof.

6. The method according to claim 1, wherein the dermatologically acceptable carrier is in the form of an oil-in-water emulsion, a water-in-oil emulsion, or a water-in-silicone emulsion.

7. The method according to claim 1, wherein the hydrophilic amino acid residue is selected from the group consisting of arginine, lysine, glutamate, aspartate, histidine, threonine, serine, glutamine, asparagine and ornithine.

8. The method according to claim 1, wherein the hydrophobic amino acid residue is selected from the group consisting of alanine, proline, glycine, tyrosine, tryptophan, phenylalanine, valine, leucine, isoleucine, methionine and cysteine.

9. The method according to claim 1, wherein the oligopeptide exhibits at least one terminal amino acid modified with a non-amino-acid organic functional group.

10. The method according to claim 9, wherein the non-amino-acid organic functional group is selected from the group consisting of an alkyl group, an acyl group, a carbohydrate, a polyether, and a fatty acid.

11. The method according to claim 1, wherein the hydrophobic amino acid block has a length of 1, 2, 3, 4, or 5 amino acids.

12. The method according to claim 1, wherein the hydrophilic amino acid block has a length of 1, 2, 3, 4, or 5 amino acids.

13. The method according to claim 1, wherein the macrostructure comprises one or more of a membrane, a film, and a macrofiber.

14. The method according to claim 4, wherein the concentration of the oligopeptide is from about 0.001% to about 0.1% by weight of the cosmetic composition.

15. The method according to claim 1, wherein the oligopeptide exhibits at least one terminal amino acid modified with a phosphate group.

\* \* \* \* \*

SEQUENCE LISTING

```
<160> NUMBER OF SEQ ID NOS: 14

<210> SEQ ID NO 1
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 2

Ala Arg Ala Asp Ala Arg Ala Asp Ala Arg Ala Asp Ala Arg Ala Asp
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 3
```

Ala Lys Ala Asp Ala Lys Ala Asp Ala Lys Ala Asp Ala Lys Ala Asp
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 4

Ala His Ala Asp Ala His Ala Asp Ala His Ala Asp Ala His Ala Asp
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 5

Ala Arg Ala Glu Ala Arg Ala Glu Ala Arg Ala Glu Ala Arg Ala Glu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 6

Ala Lys Ala Glu Ala Lys Ala Glu Ala Lys Ala Glu Ala Lys Ala Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 7

Ala His Ala Glu Ala His Ala Glu Ala His Ala Glu Ala His Ala Glu
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 8

Arg Ala Arg Ala Asp Ala Asp Ala
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 9

Arg Ala Arg Ala Arg Ala Asp Ala Asp Ala Asp Ala

```
<210> SEQ ID NO 10
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 10

Arg Ala Arg Ala Arg Ala Arg Ala Asp Ala Asp Ala Asp Ala Asp Ala
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 11

Val Val Val Ala Ala Ala Glu Glu Glu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 12

Val Val Val Ala Ala Ala Lys Lys Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic oligopeptide

<400> SEQUENCE: 13

Lys Thr Thr Lys Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic oligopeptide
<220> FEATURE:
<221> NAME/KEY: MISC_FEATURE
<222> LOCATION: (1)..(1)
<223> OTHER INFORMATION: Covalently bound to palmitoyl group

<400> SEQUENCE: 14

Lys Thr Thr Lys Ser
1               5
```